(12) United States Patent
Radmand

(10) Patent No.: US 11,471,321 B2
(45) Date of Patent: *Oct. 18, 2022

(54) HYBRID ORAL DEVICE

(71) Applicant: Achaemenid, LLC, Stratford, CT (US)

(72) Inventor: Reza Radmand, Boston, MA (US)

(73) Assignee: Achaemenid, LLC, Stratford, CT (US)

( * ) Notice: Subject to any disclaimer, the term of this patent is extended or adjusted under 35 U.S.C. 154(b) by 362 days.

This patent is subject to a terminal disclaimer.

(21) Appl. No.: 16/747,068

(22) Filed: Jan. 20, 2020

(65) Prior Publication Data

US 2020/0146875 A1 May 14, 2020

Related U.S. Application Data

(63) Continuation of application No. 15/411,124, filed on Jan. 20, 2017, now Pat. No. 10,568,757.

(60) Provisional application No. 62/353,991, filed on Jun. 23, 2016, provisional application No. 62/281,912, filed on Jan. 22, 2016.

(51) Int. Cl.
| | | |
|---|---|---|
| *A61F 5/56* | (2006.01) | |
| *A61M 16/04* | (2006.01) | |
| *A61M 16/08* | (2006.01) | |

(52) U.S. Cl.
CPC ......... *A61F 5/566* (2013.01); *A61M 16/0493* (2014.02); *A61M 16/0497* (2013.01); *A61M 16/0816* (2013.01)

(58) Field of Classification Search
CPC ........... A61M 16/0493; A61M 16/0497; A61F 5/566; A61F 5/56; A61F 2005/563; A61F 2002/046; A61F 5/08; A63B 71/085; A63B 2071/088; A63B 2071/086
See application file for complete search history.

(56) References Cited

U.S. PATENT DOCUMENTS

| | | |
|---|---|---|
| 3,139,088 A | 6/1964 | Galleher, Jr. |
| 4,304,227 A | 12/1981 | Samelson |
| 6,405,729 B1 | 6/2002 | Thornton |
| 6,571,798 B1 | 6/2003 | Thornton |

(Continued)

OTHER PUBLICATIONS

David Ireland, The Sleeping Experience, Product Description Sheet, http://www.coroflot.com/davidireland, Jul. 25, 2009, 8 pgs.

(Continued)

*Primary Examiner* — Ophelia A Hawthorne
(74) *Attorney, Agent, or Firm* — Moyles IP, LLC

(57) ABSTRACT

An oral device for treating obstructive sleep apnea is generally described. In an embodiment, the oral device includes an anchoring member, a lip sealing member and an air transmission member configured to receive and transmit air to a user. The air transmission member may divide and distribute the air to multiple locations within the user's oral cavity. The anchoring member is configured to receive a dentition of the user. According to some embodiments, the lip sealing member may include an inner lip seal and an outer lip seal. The inner and outer lip seals are customized to the user's lips and may be slidably received on the air transmission member. Thus, the lip sealing member is configured to provide a substantially airtight seal for the user's lips, thereby limiting and/or inhibiting air exchange between the user's lips.

18 Claims, 8 Drawing Sheets

(56) References Cited

U.S. PATENT DOCUMENTS

| | | |
|---|---|---|
| 6,675,802 B1 | 1/2004 | Thornton |
| 6,966,319 B2 | 11/2005 | Fitton |
| 7,137,393 B2 | 11/2006 | Pivovarov |
| 8,091,554 B2 | 1/2012 | Jiang |
| 8,893,719 B2 | 11/2014 | Lavi et al. |
| 10,568,757 B2 * | 2/2020 | Radmand .......... A61M 16/0493 |
| 2003/0150450 A1 * | 8/2003 | Fitton ...................... A62B 9/06 128/200.24 |
| 2005/0236003 A1 | 10/2005 | Meader |
| 2006/0112962 A1 | 6/2006 | Tebbutt et al. |
| 2013/0104913 A1 | 5/2013 | Evans et al. |
| 2013/0211270 A1 | 8/2013 | St. Laurent et al. |
| 2014/0276171 A1 | 9/2014 | Hestness et al. |
| 2015/0007830 A1 | 1/2015 | Remmers et al. |

OTHER PUBLICATIONS

Sleepwell Northwest, CPAP—Oral Appliance Hybridization, 4 pgs., http://www.sleepwellnorthwest.com/treatments/cpap.

Marie Marklund, et al., Non-CPAP therapies in obstructive sleep apnoea: mandibular advancement device therapy, European Respiratory Journal, Nov. 10, 11, vol. 39, No. 5., 7 pgs.

Lizette Borreli, Sleep Apnea May Increase Pneumonia Risk; CPAP May Increase Pulmonary Aspiration, Bacteria, Mar. 3, 2014, 10 pgs., http://www.medicaldaily.com/.

Norman Wolkove, et al, Long-term compliance with continuous positive airway pressure in patients with obstructive sleep apnea, Oct. 2008, 8 pg., https://www.ncbi.nlm.nih.gov/.

Shock Doctor, Shock Doctor Double Braces Strapless Mouthguard, 6 pgs., http://www.amazon.com/Shock-Doctor.

Shock Doctor, Mouthguards Chart, 1 pg., https://www.shockdoctor.com/products/mouthguards.

* cited by examiner

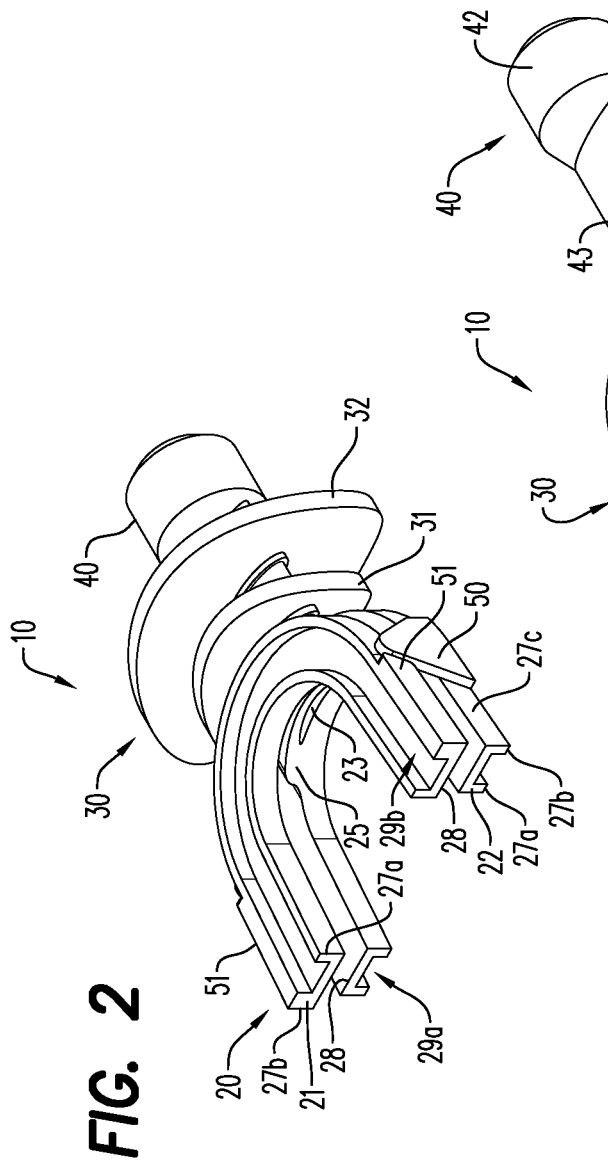
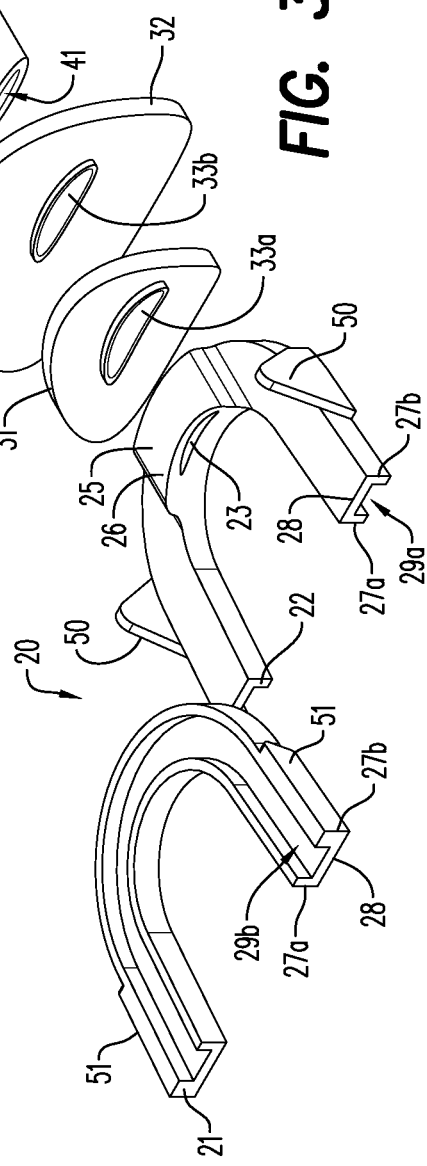

HYBRID ORAL DEVICE

CROSS-REFERENCE TO RELATED APPLICATIONS

This application is a continuation of U.S. application Ser. No. 15/411,124 filed Jan. 20, 2017, which claims the benefit of U.S. Provisional Application No. 62/353,991, filed Jun. 23, 2016, and U.S. Provisional Application No. 62/281,912, filed Jan. 22, 2016, each of which is incorporated herein by reference in its entirety.

FIELD

A device and a method for providing treatment of obstructive sleep apnea in a user including an anchoring member, a lip sealing member and an air transmission member is generally described.

BACKGROUND

Sleep apnea is a common medical condition during which a person experiences one or more pauses in breathing and/or shallow breaths during sleep. While there are several types of sleep apnea, the most common type is obstructive sleep apnea. In this medical condition, one or more of the person's throat muscles relax during sleep causing surrounding tissues in the posterior portions of the mouth, nose and throat to collapse and block the airway. Persons suffering from obstructive sleep apnea have inadequate oxygen exchange during sleep, which can lead to daytime fatigue, lack of concentration and mood changes. Left untreated, obstructive sleep apnea can have a significant impact on a person's health, often leading to cardiovascular, stroke and metabolic disorders.

Known methods for treatment of obstructive sleep apnea include both surgical and nonsurgical devices. A popular surgical procedure is uvulopalatopharyngoplasty, whereby a portion of the soft palate is removed in an effort to prevent closure of the airway by excess tissue during sleep. A disadvantage of this procedure, however, is that the operation is often expensive and may damage throat muscles necessary for swallowing and/or cause other undesirable disorders, such as, nasal regurgitation. To reduce this risk, various nonsurgical approaches have been employed. Once such nonsurgical approach includes using standardized oral appliances to incrementally advance and/or protrude the mandible (lower jaw) relative to the maxilla (upper jaw). These standardized appliances, commonly referred to as a mandibular advancement device, ("MAD"), typically include upper and lower dental trays, whereby the lower dental tray is designed to advance the mandible, and hence, move the tongue forward to increase the space in the posterior part of the throat and the oropharynx, which in turn may serve to increase the flow of air during sleep. The distance (degree of advancement) required to protrude and/or reposition the mandible may be, at least in part, dependent on the severity of the individual's obstructive sleep apnea, as well as psychological variables among the users. A disadvantage of using these standard oral appliances is that they may not sufficiently provide for and/or address individualized anatomical variances, such as difference in dental arches, dentition alignment and/or jaw flexibility. Another disadvantage is that in instances where the degree of advancement is excessive, the appliance may lead to long-term temporomandibular joint ("TMJ") disorders, muscular aggravation, dentition discomfort and/or myofascial disorders. As a result, use of these standard appliances has an approximate compliance rate of 75% over a 2-year period. For a detailed study of compliance with use of MAD, see *Non-CPAP therapies in obstructive sleep apnoea: mandibular advancement device therapy*, see Eur Respir J 2012; 39: 1241-1247, which is incorporated by reference in its entirety. Thus, such oral appliances may not treat obstructive sleep apnea in a manner that prevents and/or limits impacts on a person's health.

Other methods of treating obstructive sleep apnea include the administration of positive air pressure via a continuous positive airway pressure ("CPAP") machine. The CPAP machine is often assembled for use in combination with various face or nasal masks and may provide continuously pressurized and/or forced air during the person's sleep. A disadvantage of this assembly is that it may cause nasal and/or oral mucosal dryness due to the continuously forced air and may also cause claustrophobia due to the presence of a mask on the patient's face. As a result, use of these assemblies has an approximate compliance rate of 50% over a 5-year period. For a detailed study of compliance with use of CPAP machines, see *Long-term compliance with continuous positive airway pressure in patients with obstructive sleep apnea*, Can Respir J. 2008 October 15(7): 365-369, which is incorporated by reference in its entirety. Another disadvantage is that standard masks are not properly adapted for a customized fit for persons with unique and/or variable facial anatomies that may be natural or created by loss of muscle tone secondary to facial paralysis and/or stroke. Ill-fitting masks may lead to leakage of air and/or inadequate air intake. In addition, the masks used with CPAP machines have been found to be a breeding ground for bacteria and fungi. Despite routine washing and cleaning measures, the bacteria and fungi on these masks can grow exponentially, and lead to infections, such as pneumonia, in the airways of persons who use them. Moreover, such assemblies may not sufficiently treat obstructive sleep apnea and may fail to promote patient compliance with the treatment method.

The aforementioned treatment techniques may not provide sufficient treatment of obstructive sleep apnea, may cause and/or promote other negative health situations for the user and may not foster compliance with treatment methods.

In view of the disadvantages associated with currently available methods and devices for treating obstructive sleep apnea, there is a need for a device and method that treats obstructive sleep apnea while providing a customized individualized fit that addresses a user's anatomical variances and prevents and/or limits long-term TMJ disorders, muscular aggravation, dentition discomfort and/or myofascial disorders that may occur with continued use of oral appliances. Further, there is a need for an oral device that provides a pathway for air that treats obstructive sleep apnea by creating a customized and substantially airtight seal inside and outside or around a person's lips, while preventing and/or limiting air leakage.

BRIEF DESCRIPTION

According to an aspect, the present embodiments may be associated with an oral device for the treatment of sleep disorders, such as obstructive sleep apnea, in a user. The oral device may include an anchoring member configured to receive dentition of the user and a customized lip sealing member. The oral device may include an air transmission member configured to receive and transmit air to the user and adapted to receive the lip sealing member thereon.

BRIEF DESCRIPTION OF THE FIGURES

A more particular description will be rendered by reference to specific embodiments thereof that are illustrated in the appended drawings. Understanding that these drawings depict only typical embodiments thereof and are not therefore to be considered to be limiting of its scope, exemplary embodiments will be described and explained with additional specificity and detail through the use of the accompanying drawings in which:

FIG. 2 is a perspective view of an oral device having upper and lower anchoring members, according to an embodiment;

FIG. 3 is an exploded perspective view of the oral device of FIG. 2 showing the oral device in an unassembled manner;

Figure 1B:
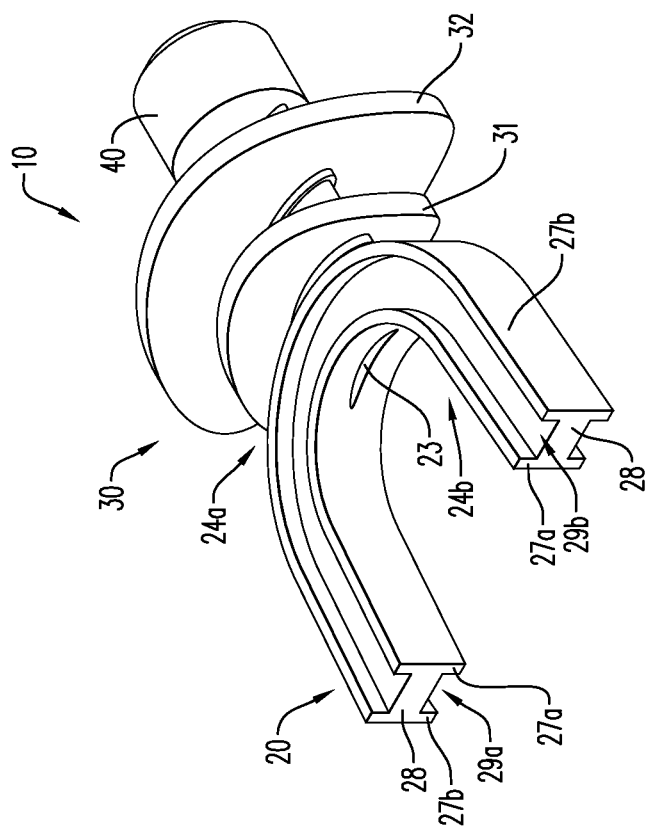
FIG. 1B is a perspective view of an oral device, illustrating an anchoring member configured as a unitary structure to receive an upper dentition and a lower dentition of a user, according to an embodiment.

Various features, aspects, and advantages of the embodiments will become more apparent from the following detailed description, along with the accompanying figures in which like numerals represent like components throughout the figures and text. The various described features are not necessarily drawn to scale, but are drawn to emphasize specific features relevant to some embodiments.

DETAILED DESCRIPTION

Reference will now be made in detail to various embodiments. Each example is provided by way of explanation, and is not meant as a limitation and does not constitute a definition of all possible embodiments.

Embodiments of the disclosure relate generally to devices and methods for treating obstructive sleep apnea, as well as a device for inhibiting and/or limiting snoring that may be caused by obstructive sleep apnea. Such devices provide particular utility in providing a customized and/or individualized fit that addresses a user's anatomical variances. The oral device contemplated includes an anchoring member configured to receive a dentition of the user, a lip sealing member coupled to the anchoring member and an air transmission member adapted to receive the lip sealing member thereon and configured to receive and transmit air to the user. For example, the oral device described herein may include customizable materials that provide a comfortable fit for a user and at least limits and/or inhibits leakage of air when in use. The oral device contemplated may treat obstructive sleep apnea and/or increase user compliance rates.

According to an aspect, the anchoring member may be customized to at least one of the upper and lower dentition of the user, thereby providing a comfortable fit that enhances the user's comfort and/or increases the user's likelihood of repeated and consistent use, i.e., the user's compliance rate. The anchoring member may include a mandibular advancement member capable of providing minimal mandible advancement, thereby reducing the user's risk of developing long-term TMJ disorders, muscular aggravation, dentition discomfort and/or myofascial disorders. In an embodiment, the lip sealing member of the oral device may include an inner lip seal and an outer lip seal, wherein each of the inner and outer lip seals includes an orifice extending therethrough. According to an aspect, the inner and outer lip seals are customized to the lips of the user and may be adjustable toward and away from the anchoring member, thereby creating a substantially airtight seal inside the user's lips and outside the user's lips. Thus, the oral device is capable of creating a customized seal both inside and outside or around the user's lips, which may at least limit and/or inhibit leakage of air provided by the air transmission member. As such, the oral device functions as a hybrid oral device, capable of being customizable to the user's dentition and the lips/mouth of the individual user.

For purposes of illustrating features of the embodiments, various examples will now be introduced and referenced throughout the disclosure. Those skilled in the art will recognize that these examples are illustrative and not limiting and are thus provided purely for explanatory purposes.

Figure 1A:
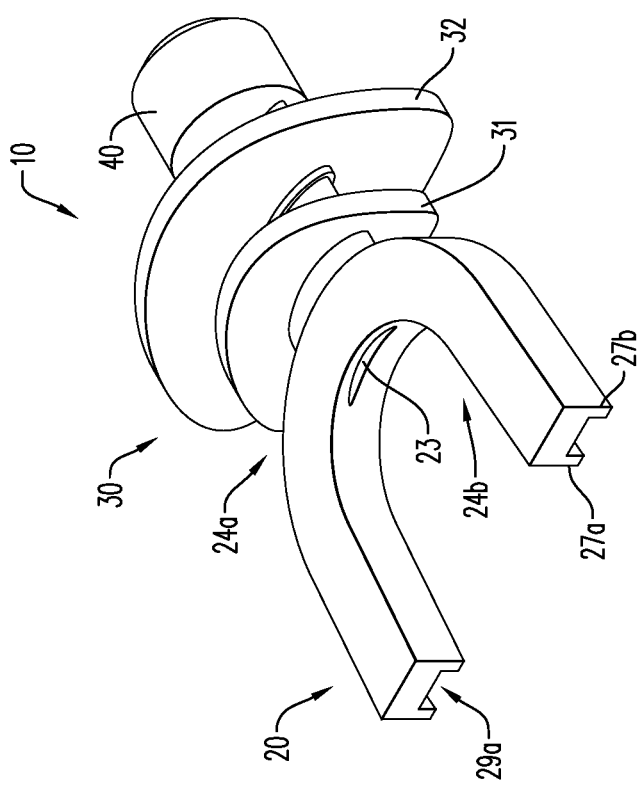
FIG. 1A is a perspective view of an oral device, illustrating an anchoring member configured as a unitary structure to receive a lower dentition of a user, according to an embodiment.
Figure 9:
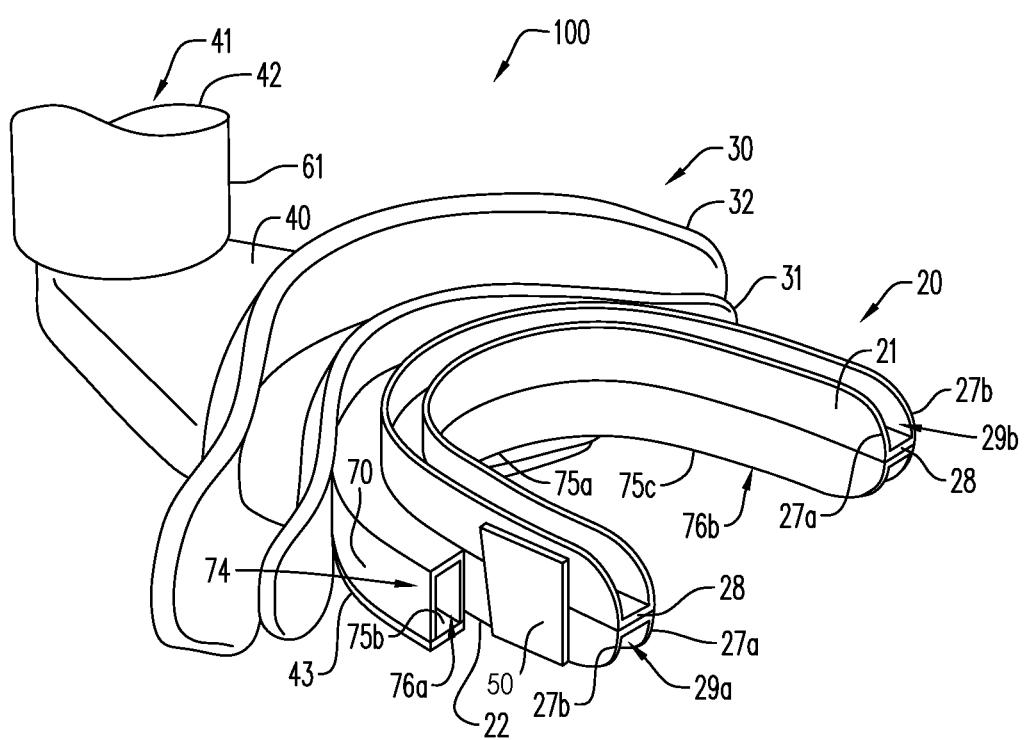
FIG. 9 is a perspective view of an oral device according to an embodiment.

In an embodiment, and with particular reference to FIGS. 1A-1B and 9, an oral device 10/100 for treatment of sleep apnea in a user is provided. The oral device 10/100 is illustrated having an anchoring member 20, a lip sealing member 30 coupled to the anchoring member 20 and an air transmission member 40 adapted to receive the lip sealing member 30 thereon. According to an aspect, the lip sealing member 30 includes an inner lip seal 31 and an outer lip seal 32, described in further detail hereinbelow. The oral device 10 may be adapted and configured to receive airflow from a pressurized airflow machine 60. (See, for example, FIG. 7.) Although FIG. 1A illustrates the anchoring member 20 for receiving only one dentition, i.e. the lower dentition, it is to be understood that in some configurations, the anchoring member 20 may be for only the upper dentition. In some embodiments, the anchoring member 20 may be for both the upper dentition and the lower dentition (see, for example, FIGS. 1B and 9). In some embodiments, the anchoring member 20 may be provided in generic sizes, (similar to a sports mouth guard), such as small, medium, large or extra-large.

In an embodiment, the anchoring member 20 is customized to the dentition of the user in a manner that provides for a comfortable fit to the user's dentition. When customized, the anchoring member 20 can be formed of self-conforming materials that are adaptable to changes in mouth structure, or through use of a dental impression of the individual user's dentition, as would be understood by one of ordinary skill in the art. A dental impression is a negative imprint of hard (teeth) and soft tissues in the individual user's mouth from which positive reproduction (or cast) can be formed. Thus, the anchoring member 20 can be custom manufactured using materials commonly available to fit to the individual user's dentition from the cast of their own teeth.

The type of material selected to form the anchoring member 20 would be known to one of ordinary skill in the art and includes polymers, thermoplastics, acrylics, silicone, rubber, or any other material that can be used to form the anchoring member 20 conformed to the user's teeth. In an embodiment, the materials are medical-grade, latex-free, BPA-free and any other material known to minimize patient health risks. According to an aspect, the anchoring member 20 may be formed from the impression made in a thin, resilient material.

According to an aspect, the anchoring member 20 includes a tray having dentition receiving cavities (not shown) shaped and sized to receive at least one or more dentition of the user. The dentition receiving cavities may have a shape that is substantially the same as the shape of dentition for which it has been molded and/or shaped to fit. In this configuration, the anchoring member 20 is capable of being at least temporarily fixed in place by way of being molded and conformed to the dentition of the user, thus providing the customized fit. Thus, the anchoring member 20 may provide an anchoring function, thereby allowing the oral device 10/100 to remain in place during the user's sleep, particularly in situations where the user may make slight to moderate movements during sleep and/or when the user may be awake. As such, the anchoring member 20 becomes substantially immovable unless positive effort is applied to remove the anchoring member 20. In other words, the user may remove the anchoring member 20 at any time, if desired. Since the anchoring member 20 is not permanently affixed to the dentition, it can be worn and/or subsequently removed by the user at any time. Therefore, the oral appliance 10/100 may be used for varying lengths of time.

Figure 8:
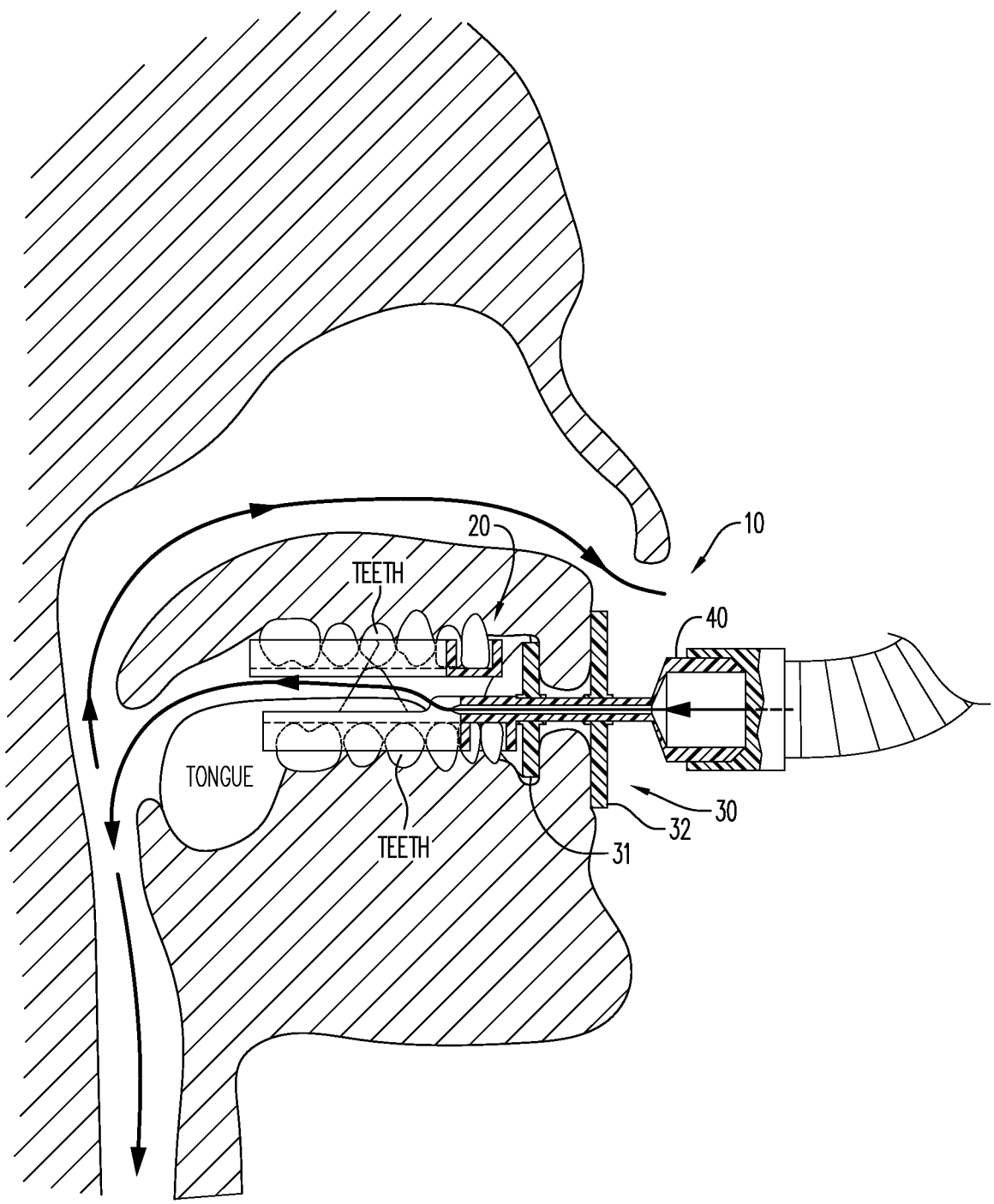
FIG. 8 is a cross-sectional side view of an oral device being worn by a user, according to an embodiment.

As illustrated in FIG. 1A, the anchoring member 20 may be configured to receive the lower dentition of the user (see, for instance, FIG. 8). The anchoring member 20 may include a base portion 28, an inner wall 27a and an outer wall 27b. Each of the inner and outer walls 27a, 27b may extend from a periphery of the base portion 28. Thus, the inner wall 27a extends adjacent to at least a portion of a lingual surface of the teeth, i.e. between the teeth and the tongue (for instance), while the outer wall 27b extends adjacent to at least a portion of a buccal surface of the teeth, i.e. between the teeth and the cheek. When in use, the base portion 28 may extend over and/or cover the occlusal or dentition bite surfaces of the teeth, and the inner and outer walls 27a, 27b at least partially cover the buccal and lingual dentition surfaces, respectively. In other words, the lower dentition may be received in a mandibular channel 29a bounded by the inner and outer walls 27a, 27b extending from the periphery of the base portion 28. The anchoring member 20 may further include an aperture 23 positioned anteriorly (for example, near the opening of the mouth), and extending from a buccal position 24a to a lingual position 24b through the anchoring member 20. Alternatively, in another embodiment (not shown), the air transmission member 40 may be attached to the base portion 28 of the anchoring member 20. According to an aspect, when the anchoring member 20 is positioned on and/or over the lower dentition of the user, the aperture 23 is connectable to the air transmission member 40 and is adapted to receive air therefrom. When the oral device 10 is in use, air can enter and/or exit the user's mouth by way of the air being provided via the transmission member 40 and being received through the aperture 23 of the anchoring member 20. As illustrated in FIG. 1A, a lip sealing member 30 having an inner lip seal 31 and an outer lip seal 32 may be provided. The inner and outer lip seals 31, 32 may be positioned on the air transmission member 40 and may provide an airtight seal for the user's lips (shown and described in further detail hereinbelow).

In an embodiment and as illustrated FIGS. 1B and 9, the anchoring member 20 is configured to receive both the upper and lower dentition (not shown) of the user. In this configuration, the anchoring member 20 may include the inner wall 27a and the outer wall 27b that extend laterally from the periphery of the base portion 28. In this configuration, the inner and outer walls extend in both directions (e.g. up and down) from the base portion, forming a substantial H-shape, and in some views a substantial I-shape. In this embodiment, the upper dentition may be received in a maxillary channel 29b and lower dentition may be received in the mandibular channel 29a. As illustrated in FIG. 1B and according to an aspect, the aperture 23 may extend through the base portion 28, by virtue of being an opening that extends from the buccal position 24a to the lingual position 24b of the anchoring member 20. According to an aspect, the anchoring member 20 may be arranged as a unitary structure configured to receive the user's upper and lower dentition, thereby providing additional support and anchoring effect to keep the oral device 10/100 in place. The dentition receiving cavities (not shown) may provide and/or facilitate at least temporarily holding the anchoring member 20, and therefore the oral device 10/100, in place.

In an embodiment and as illustrated in FIGS. 2-3 and 9, the anchoring member 20 includes separate upper member 21 and lower member 22. The upper and lower members 21, 22 may each include base portions 28, inner walls 27a and outer walls 27b. Each of the inner walls 27a and the outer walls 27b may extend in one direction from the periphery of the base portion 28, thereby providing the respective maxillary channels 29b and mandibular channels 29a for receiving the upper and the lower dentition of the user. According to an aspect, the lower member 22 includes a mandibular protrusion member 50 extending bilaterally from the buccal surface 27c of the outer wall 27b. As illustrated in FIG. 2, the mandibular protrusion members 50 of the lower member 22 may be angled in a manner that engages with bilateral displacers 51 positioned posteriorly on the buccal surface 27c of the upper member 21. When in use, the mandibular protrusion member 50 provided with the bilateral displacers 51 is configured to at least slightly fulcrum or move the mandible in a forward direction, i.e., anteriorly towards the opening of the user's mouth, as would be understood by one of ordinary skill in the art of the aforementioned MAD. While the mandibular protrusion members 50 are depicted as working in concert with bilateral displacers 51, any modality as would be contemplated by one of ordinary skill in the art may be utilized to perform the function of moving the mandible in a slightly forward direction. In other words, if the natural position of opposing teeth of the upper and lower dentition of the user generally contact each other at their surfaces (for instance, the surfaces of teeth that touch the naturally opposing teeth surfaces when the mouth is at rest or in a closed position), the mandibular protrusion member 50 may at least slightly advance the mandible so that the naturally opposing teeth surfaces are no longer in contact and the lower dentition extends more anteriorly than the upper dentition. The mandibular protrusion member 50 may keep the user's mandible slightly advanced so that the tongue of the user does not impede air transported from the air transmission member 40 and received through the aperture 23. According to an aspect, the air is sealed in by the inner and outer lip seals 31, 32 of the lip sealing member 30 and leakage of the air is at least limited and/or inhibited.

According to an aspect and as illustrated in FIGS. 2 and 3, the anchoring member 20 may include an air conduit 25 having the aperture 23 formed therein. As shown in more detail in FIG. 3, the air conduit 25 may include a conduit body 26 connected to the air transmission member 40. In an embodiment, the conduit body 26 is slightly raised relative to the base portion 28 of the lower member 22. The conduit body 26 may be formed integrally with the lower member 22. Alternatively, the conduit body 26 may be slightly raised relative to the base portion 28 of the upper member 21, and be integrally formed therewith. Alternatively, in another embodiment, the conduit body is a separate unit that is connected or fastened to the base portion 28 of the lower member 22, as would be contemplated by one of ordinary skill in the art. Thus, the conduit body 26 may be secured by adhesive, a mechanical fastener or any other securing mechanism sufficient to hold the conduit body 26 in place, particularly during repeated use. In any event, the securing mechanism selected may be chosen so it does not interfere with the comfortable and customized fit of the anchoring member 20. According to an aspect, the conduit body 26 is sized and positioned to keep the user's mouth slightly ajar during sleep. In an embodiment, the conduit body 26 is removably attached to the anchoring member 20 to allow for ease of replacement of the anchoring member 20.

Figure 7:
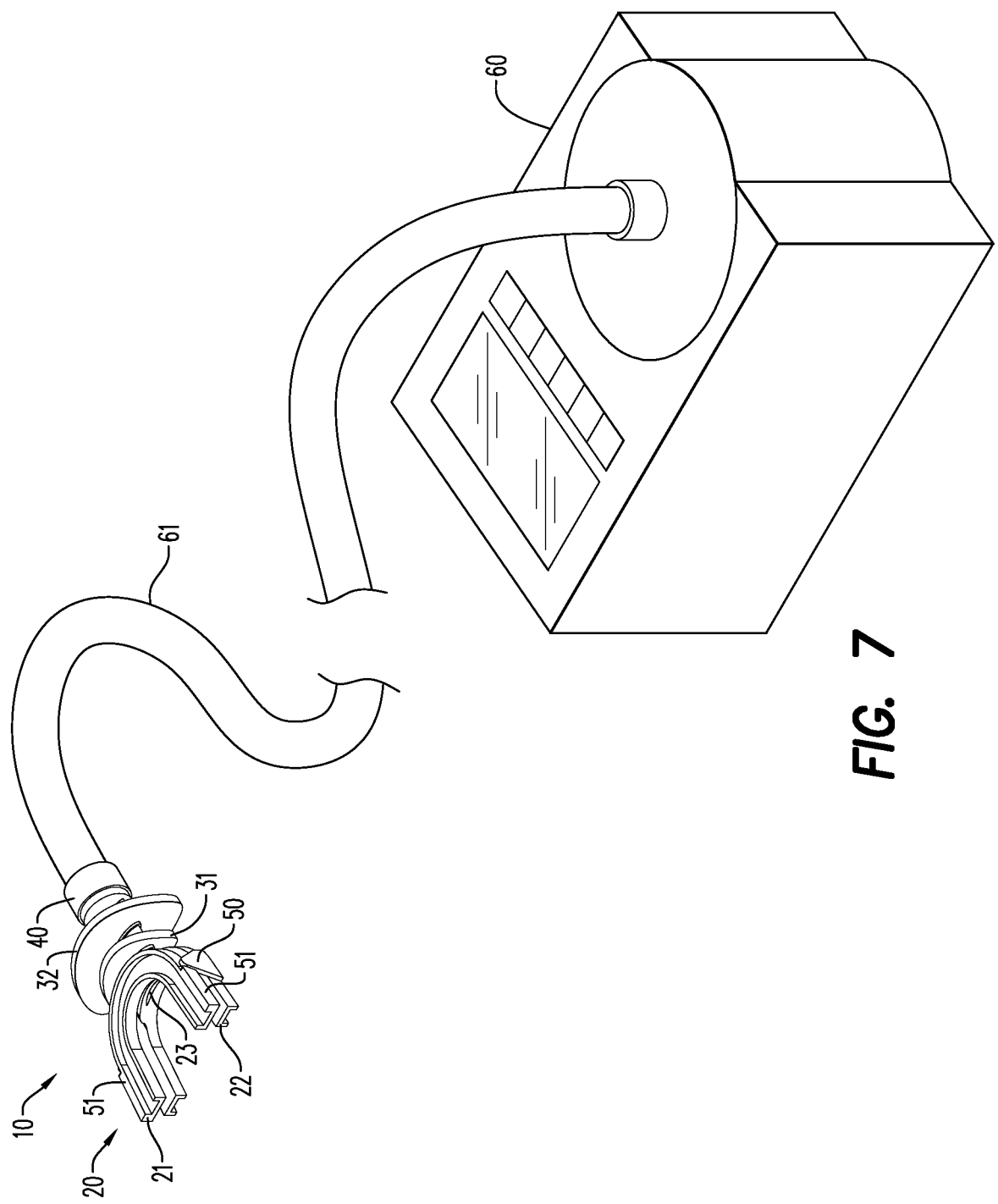
FIG. 7 is a perspective view of an oral device attached to a pressurized airflow machine, according to an embodiment.

As illustrated in FIG. 3, the air transmission member 40 may include a passageway 41 configured to receive air and transmit air to the user. According to an aspect, the passageway 41 extends from a receiving end 42 to a delivery end 43 of the air transmission member 40. The receiving end 42 is shaped and sized to receive an air hose or other air delivery mechanisms (see, for instance, FIGS. 7 and 11), that is, the receiving end 42 is configured to function as an air inlet. According to an aspect, and as illustrated in FIG. 7, the delivery end 43 of the air transmission member 40 of the oral device 10 may be shaped and sized to connect to and be in air-transmissible communication with the orifice 23 of the anchoring member 20, such that at least a portion of the delivery end 43 is capable of being received within the user's mouth. In an embodiment, the delivery end 43 of the air transmission member 40 is connected to the anchoring member 20 by a coupling mechanism or other retention means (not shown). According to an aspect, the air transmission member 40 is fixed to the anchoring member 20. The air transmission member 40 may be removably connected to the anchoring member 20. In an embodiment, air supplied through the passageway 41 of the air transmission member 40 is directed through the passageway 41 and into the user's mouth. The passageway 41 may be of any size and/or shape capable of receiving and transmitting air to the user. The air transmission member 40 is adapted and configured to form an airtight seal when coupled to the anchoring member 20. According to an aspect, the receiving and delivery ends 42, 43 each include attachment mechanisms (not shown) having one or more of a mounting flange, a gasket, and seals. Substantially no air or a limited amount of air is leaked when the lip sealing member 30 and the anchoring member 20 are arranged to create a substantially airtight seal for the user's lips. While the air transmission member 40 is illustrated as having a substantially cylindrical body at the receiving end 42, and a substantially cylindrical body having a generally oval shaped at the delivery end 43, it is to be understood that the air transmission member 40 may be of any shape and/or size that is capable of receiving inner and outer lip seals 31, 32 thereon.

With reference to all of the figures, the lip sealing member 30 will now be described. In an embodiment, the lip sealing member 30 includes an inner lip seal 31 configured and adapted to be positioned between the teeth of the user and the inside of the user's lips, at the opening of the user's mouth, and an outer lip seal 32 configured and adapted to be positioned outside the user's lips. The lip sealing member 30 may be slidably received on the air transmission member 40. According to an aspect, the inner and outer lip seals 31, 32 are designed to work in conjunction to provide an airtight seal for the lips of the user. In an embodiment, the inner lip seal 31 and the outer lip seal 32 are each custom fabricated to conform to the shape of both the inside and outside of the individual user's lips. In any event, the inner lip seal 31 works in concert with the outer lip seal 32 to provide an airtight seal that substantially limits and/or inhibits air received from the air transmission member 40 from escaping from the inside and/or the outside of the user's lips. (See, for example, FIGS. 8 and 11.) According to an aspect, at least one of the inner lip seal 31 and the outer lip seal 32 is composed of an initially soft-moldable material that is curable into a semi-rigid material. When cured, the soft-moldable material may provide a customized fit for the user. According to an aspect, the soft-moldable material is a biocompatible material, such as a polymer, that is configured to be in contact with human tissue and bodily liquids, including saliva. The inner and outer lip seals 31, 32 may include rubber, silicone, polyetheretherketone (PEEK), polyurethane, latex or any combination thereof. The material selected for creating the inner and outer lip seals 31, 32 may be selected based on the desired rigidity of the inner and outer lip seals 31, 32 and/or desired cure time. Similar to the anchoring member, the lip sealing member can be made of materials that are medical-grade, latex-free, BPA-free and any other material known to minimize patient health risks.

In an embodiment and as illustrated in FIG. 3, the inner and outer lip seals 31, 32 include respective orifices 33a, 33b, extending therethrough. Each orifice 33a, 33b, is sized to receive and/or communicate with the delivery end 43 of the transmission member 40. While the orifices 33a, 33b are shown as shaped as a substantially circular or oval configuration, it is to be understand that the orifices 33a, 33b may be shaped and sized to fit over the delivery end 43 of the air transmission member 40, according to an aspect. When positioned on the air transmission member 40, the inner and outer lip seals 31, 32 may be compressively held in place thereon.

Figure 4:
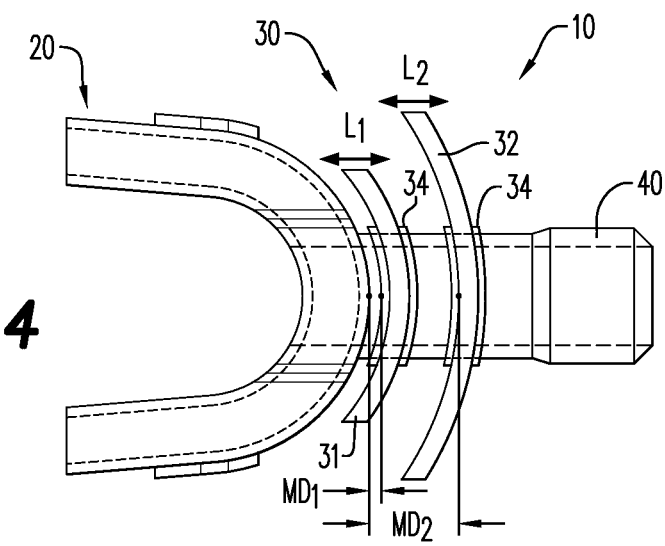
FIG. 4 is a top view of an oral device, illustrating individualized movements of inner and outer lip seals of a lip sealing member, according to an embodiment.
Figure 5:
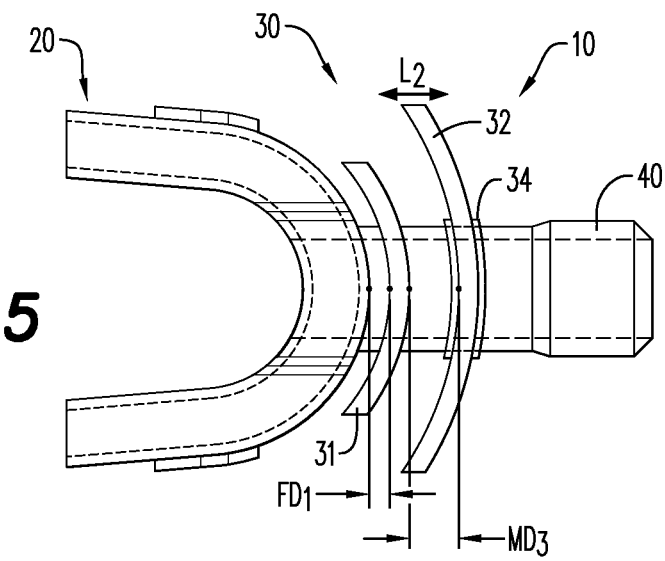
FIG. 5 is a top view of an oral device, illustrating movement of an outer lip seal of a lip sealing member, according to an embodiment.
Figure 6:
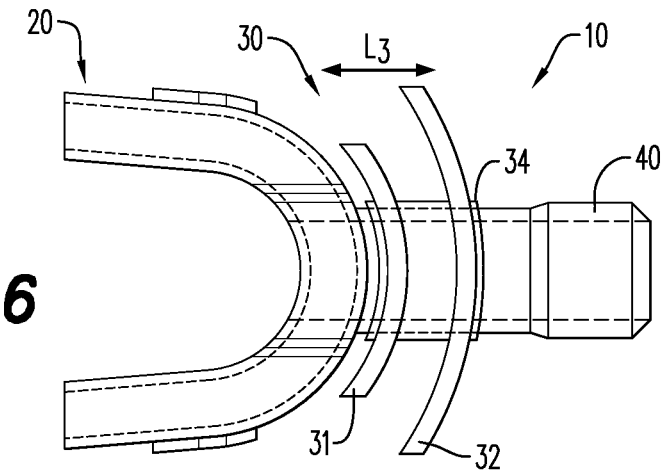
FIG. 6 is top view an oral device, illustrating the movement of the lip sealing member according to an embodiment.

As illustrated in FIGS. 4, 5 and 6, according to an aspect, at least one of the inner and outer lip seals 31, 32 may be provided with an adjustment member 34 configured to move and position the inner lip seal 31 and the outer lip seal 32 towards and away from the user's lips in a substantially air-tight relationship with the individual user's mouth/lips. The adjustment member 34 may be slidably adjusted toward and/or away from the anchoring member 20. The adjustment member 34 may be positioned on and received by the delivery end 43 of the air transmission member 40. According to an aspect, the adjustment member 34 is positioned between the air transmission member 40 and the lip sealing member 30, such that the adjustment member 34 forms the orifices 33a, 33b of at least one of the inner and outer lip seals 31, 32, respectively. In some embodiments, an adjustment member 34 is not provided, i.e., each of the inner and outer lip seals 31, 32 of the lip sealing member 30 may be in direct contact with and/or directly attached to the air transmission member 40.

In an embodiment, and as illustrated in FIG. 4, each of the inner and outer lip seals 31, 32 are individually slidably received on the air transmission member 40. As illustrated, the inner lip seal 31 may be configured to move in a lateral direction $L_1$ toward and/or away from the anchoring member 20. In other words, the inner lip seal 31 may be movable from an initial position to a final position that defines a movable or adjustable distance $MD_1$. According to an embodiment, the inner lip seal 31 can be moved towards or away from the user's lip such that the inner lip seal 31 will apply little to no force on the user's lips. Thus, the inner lip seal 31 can be moved closer to or away from the anchoring member 20 in a manner that the lips of the user are naturally relaxed, rather than protruded and/or anteriorly extended to provide flexibility of optimal fit based on the anatomical features of each individual user.

According to an aspect and as illustrated in FIG. 4, the outer lip seal 32 is similarly configured to move in a lateral direction $L_2$ toward and/or away from the anchoring member 20. In other words, the outer lip seal 32 may be movable from an initial position to a final position that is defined by a movable distance $MD_2$. According to an embodiment, the outer lip seal 32 can be moved towards or away from the user's lips such that the outer lip seal 32 will apply little to no force on the user's lips. Thus, the outer lip seal 32 can be moved closer to or away from the anchoring member 20 in a manner that the lips of the user are naturally relaxed, rather than protruded and/or anteriorly extended to provide flexibility of optimal fit based on the anatomical features of each individual user.

According to an aspect and as illustrated in FIG. 5, the outer lip seal 32 is adjustably positioned on the air transmission member 40 and the inner lip seal 31 (respective inner lip seal 31) is fixed in place on the air transmission member 40. In an embodiment, the outer lip seal 32 is slidingly moveable in the lateral direction $L_2$ towards and away from the anchoring member 20. According to an embodiment, the outer lip seal 32 is adjustable on the air transmission member 40 by virtue of being slidably received thereon. The outer lip seal 32 may be movable from its initial position to its final position, while the respective inner lip seal is positioned at a fixed distance $FD_1$ away from the anchoring member 20, thereby defining the movable distance $MD_3$. When positioned closer to the respective inner lip seal 31, the outer lip seal 32 is capable of providing an airtight seal when the oral device 10 is in use. By virtue of being positioned closer to the lips of the user, the outer lip seal 32 may at least slightly compress the lips of the user, thereby at least limiting and/or inhibiting air provided by the air transmission member 40 such that air received therefrom is directed into the mouth of the user. (See, for instance, FIG. 11.) Alternatively, and in an embodiment, the inner lip seal 31 is adjustably positioned on the air transmission member 40 and the outer lip seal 32 (respective outer lip seal 32) is fixed in place on the air transmission member 40 (not shown). In this configuration, the inner lip seal 31 may be slidingly moveable in the lateral direction $L_1$ towards and away from the respective outer lip seal 32. According to an aspect, when the inner lip seal 31 is moved towards the anchoring member 20, it is moved further away from the respective outer lip seal 32, thereby reducing any compressive force and/or pressure applied to the inside of the user's lips during use. In an embodiment, when the inner lip seal 31 is moved away from the anchoring member 20, it is moved closer to the respective outer lip seal 32, thereby being able to and/or increasing the compressive force and/or pressure applied to the inside of the user's lips during use. In this configuration, the lip sealing member 30 may provide a substantially airtight seal.

In an embodiment and as illustrated in FIG. 6, the inner lip seal 31 and the outer lip seal 32 are positionally fixed relative to each other. According to an aspect, the inner and outer lip seals 31, 32 of the lip sealing member 30 may be customized to the lips of the individual user. The distance between the inner lip seal 31 and the outer lip seal 32 may be fixed, at least in part based on the distance between inside and outside surfaces of the user's lips as measured and fitted to the individual user. According to an aspect, the inner and outer lip seals 31, 32 are coupled to each other by a connecting means, which may be, for example, the adjustment member 34 (described in further detail hereinabove) positioned on the air transmission member 40 and sized to receive both the inner lip seal 31 and the outer lip seal 32. The inner and outer lip seals 31, 32 may be slidably received and/or move together in tandem, i.e., for instance, as a single unit, on the air transmission member 40. According to an aspect, the inner lip seal 31 and the outer lip seal 32 are both slidingly moveable in a lateral direction $L_3$ towards and away from the anchoring member 20, such that the user can adjust the customized lip sealing member 20 in a manner that provides a customized airtight seal and, when in use, provides the user with a comfortable fit.

In yet a further embodiment in which the lip sealing member 20 is custom-fit to the individual user's mouth, each of the inner lip seal 31 and the outer lip seal 32 is fixed in place (not shown) on the air transmission member 40 at the optimal distance away from the anchoring member 20 to afford the user a personalized fit. Thus, the inner lip seal 31 the outer lip seal 32 are customizably arranged in a fixed position based on the user's lips and/or the desired airtight seal. In this configuration, the user does not have to adjust the inner lip seal 31 and/or the outer lip seals 32 in order to create a customized fit. Rather, the inner and outer lip seals 31, 32 may be molded to capture the shape and distance between the inside and outside of the user's lips, respectively, and are thereafter placed on the air transmission member 40 at fixed distance sufficient to facilitate the desired airtight seal. The inner and outer lip seals 31, 32 may otherwise be held in place on the air transmission member 40 using various retention means as would be understood by a person of ordinary skill in the art. According to an aspect, at least one of the inner and outer lip seals 31, 32 may be retained on the air transmission member by virtue of being compression/press fitted thereon.

Figure 11:
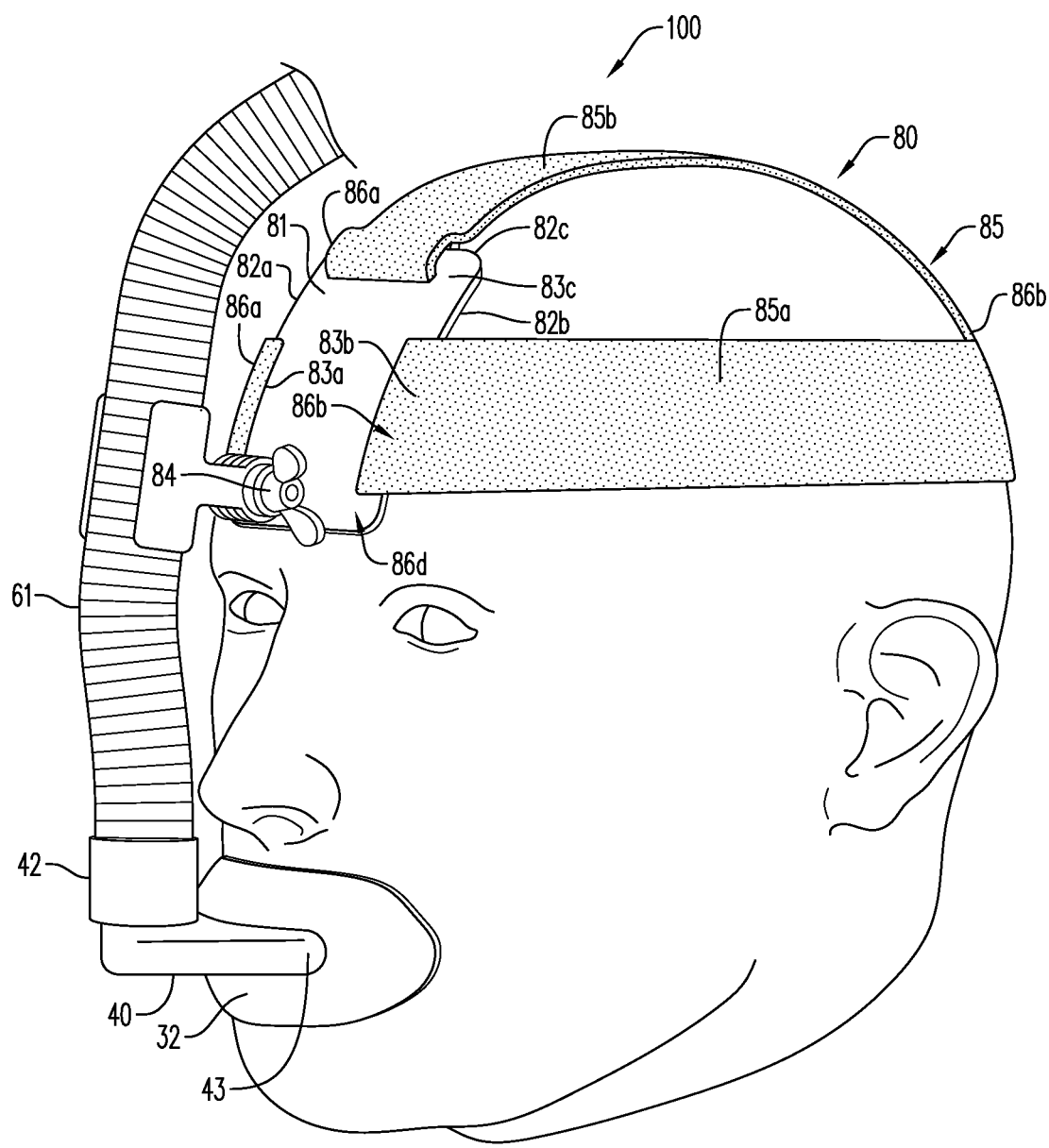
FIG. 11 is a perspective view of the oral device of FIG. 9 coupled to a headgear and being worn by a user, according to an embodiment.

According to an aspect and as illustrated in FIGS. 7 and 11, the oral device 10 is adapted for receiving airflow from a pressurized airflow machine 60. According to an aspect, the anchoring member 20, including at least one or both of the upper member 21 for receiving the upper dentition and the lower member 22 for receiving the lower dentition, is coupled to the air transmission member 40 with the lip sealing member 30 positioned therebetween. The receiving end 42 (shown in FIG. 3 and described in further detail hereinabove) of the air transmission member 40 is coupled to the pressurized airflow machine 60. The anchoring member 20 may or may not include the mandibular protrusion member 50 (described in further detail hereinabove). According to an aspect, the pressurized airflow machine 60 provides constant air pressure through a hose 61 connected to the air transmission member 40. The air provided by the pressurized airflow machine 60 is directed to the user's mouth by virtue of being supplied through the hose 61 and being transported through the air transmission member 40. The lip sealing member 30, including the inner lip seal 31 and the outer lip seal 32, may provide an airtight seal so that substantially all of the air provided by the pressurized airflow machine 60 is delivered to the user while the anchoring member 20 provides a means for passage of the air into the mouth of the user.

Figure 10A:
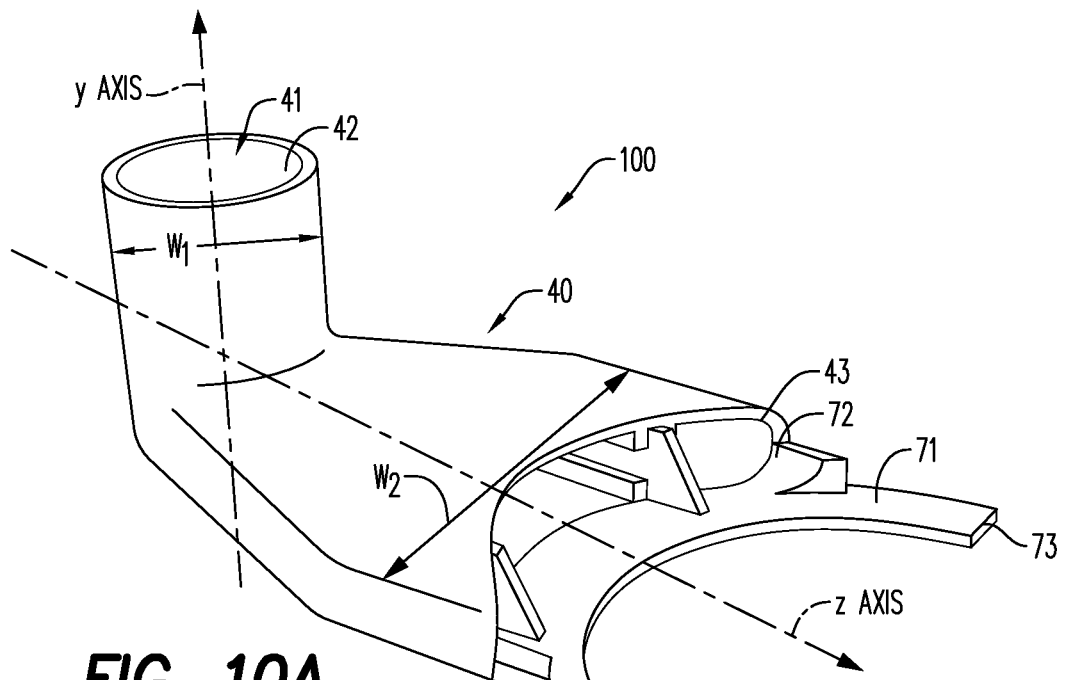
FIG. 10A is a partial perspective view of the oral device of FIG. 9, illustrating an air transmission member.
Figure 10B:
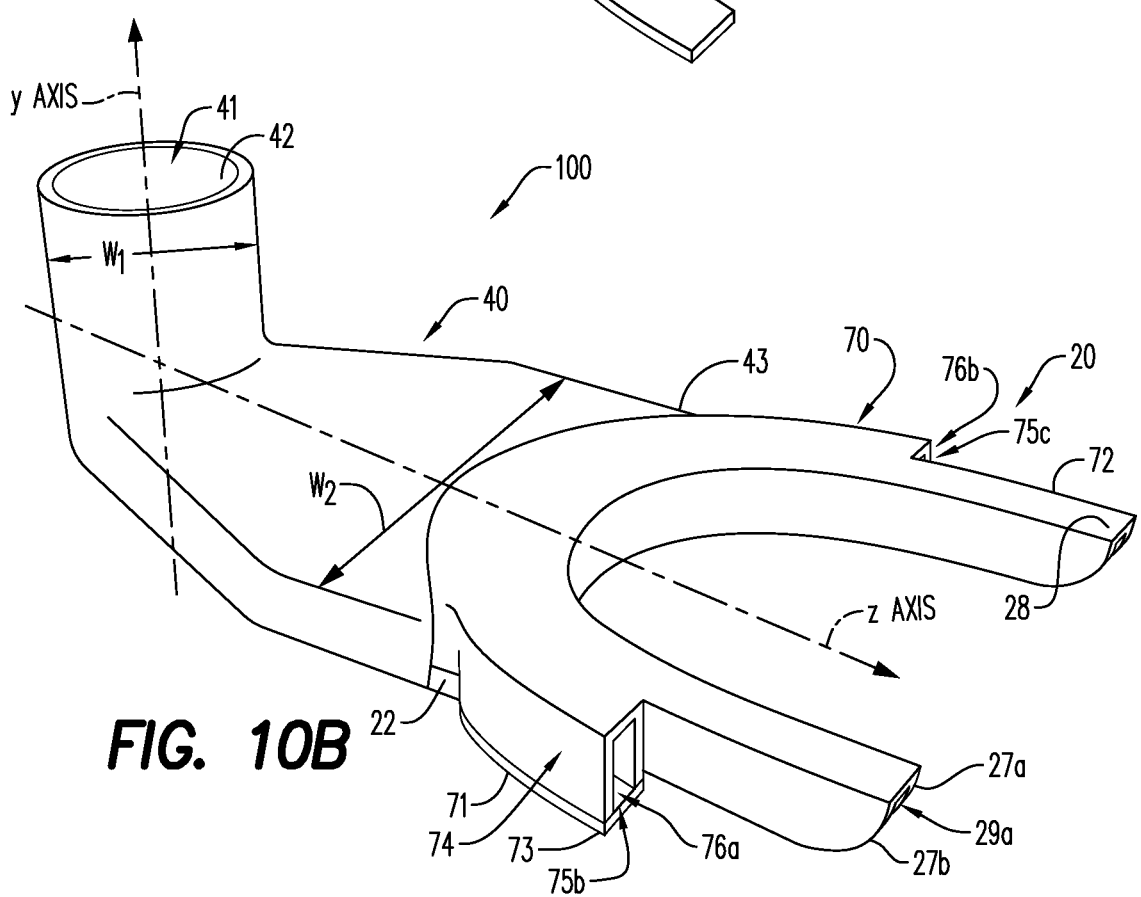
FIG. 10B is a partial perspective view of the oral device of FIGS. 9 and 10A, illustrating the air transmission member coupled to an airflow manifold.

According to an aspect, and as illustrated in FIGS. 9 and 10A-10B, the oral device 100 may further include an airflow manifold 70. The airflow manifold 70 may be positioned between the air transmission member 40 and the anchoring member 20. In an embodiment, the airflow manifold 70 is configured to separate or divide the incoming airflow into multiple streams, which are then delivered to different parts of the user's oral cavity (e.g., via openings 75a, 75b, 76b discussed below). By doing so, the overall volume of air delivered to the user's oral cavity is more evenly distributed throughout the user's oral cavity, which may help to reduce and/or eliminate nasal and/or oral mucosal dryness often resulting from continuously pressurized and/or forced air being provided to the user during the user's sleep.

As illustrated in FIGS. 10A-10B, the air transmission member 40 of the oral device 100 may include various widths. In an embodiment, the receiving end 42 and the delivery end 43 of the air transmission member 40 each have respective widths W1, W2. According to an aspect, the width W2 of the delivery end 43 is larger than the width W1 of the receiving end 42. When air is distributed through the hose 61 (see FIG. 11) to the receiving end 42 of the air transmission member 40, the air may have a first/initial velocity at the receiving end 42 that is greater than a second/resultant velocity of air at the delivery end 43. In other words, the delivery end 43 of the air transmission member 40 may be a dilated delivery end 43, in that the passageway 41 increases from the receiving end 42 to the delivery end 43 in such a manner that at the delivery end 43, the resultant velocity of air decreases, which may help reduce and/or substantially eliminate nasal and/or oral mucosal dryness.

According to an aspect and as illustrated in FIGS. 10A-10B, the airflow manifold 70 includes a connector 71 having a first end 72 and second end 73. The first end 72 of the connector 71 may be coupled to the delivery end 43 of the air transmission member 40. According to an aspect, the first end 42 of the connector 71 is positioned at the delivery end 43 of air transmission member 40 and is receivably positioned within the passageway 41 of the air transmission member 40, such that the connector 71 is securely coupled to the air transmission member 40. According to an aspect, an air tight seal is formed at the points of connection between the connector 71 and the air transmission member 40, which may help prevent any loss of air being delivered to the oral cavity of the user. Alternatively, in another embodiment (not shown), the connector 41 may be integral with the air transmission member 40, such that the connector 41 is a portion (i.e., a connector portion) of the air transmission member 40.

As illustrated in FIG. 10B, the second end 73 of the connector 71 may be coupled to the lower member 22 of the anchoring member 20. According to an aspect, the second end 73 is coupled to the outer wall 27b of the lower member 22 in a manner that forms an airtight seal at the point of connection, which helps to eliminate and/or reduced the loss of air being delivered and/distributed by the airflow manifold 70 to the user. Alternatively, in another embodiment (not shown), the connector 41 may be integral with the lower member 22 of the anchoring member 20. In such a case, the integral lower member 22/connector 41 may be coupled to the air transmission member 40, as described above. Alternatively, in yet another embodiment (not shown), the lower member 22, the connector 41, and the air transmission member 40 may all be integral with one another such that the various parts form a unitary body.

Still viewing FIGS. 9 and 10B, the oral device 100 may include a manifold body 74. According to an aspect, the manifold body 74 includes a first opening 75a, a second opening 75b and a third opening 75c. As illustrated in FIG. 9, the first opening 75a may be positioned anteriorly to the mouthpiece 20, while the second opening 75b and the third opening 75c may each be positioned substantially posteriorily to the mouthpiece 20. The body 74 may include a first deflector channel 76a extending between the first opening 75a and the second opening 75b, and a second deflector channel 76b extending between the first opening 75a and the third opening 75c. Each of the deflector channels 76a, 76b may be configured to distribute a portion of the total volume of air to the oral cavity of the user via openings 75b, 75c in conjunction with opening 75a. According to an aspect, the manifold body 74 and the connector 71 at least partially encase the deflector channels 76a, 76b in such a manner that an airtight seal is provided at all locations of the manifold body 74, other than each of the openings 75a, 75b, 75c. According to an aspect, the manifold body 74 is coupled to the connector 71. Alternatively, in another embodiment, the manifold body 74 is formed as an integral part of the lower member 22 of the anchoring member 20.

FIGS. 8 and 11 illustrate the oral device 10/100 being worn by the user, according to an embodiment. The anchoring member 20 may be customized to retain the lower dentition of the user. In an embodiment, the anchoring member 20 may be configured to retain both the upper and the lower dentition. The anchoring member 20 may include the mandibular protrusion members 50 (shown in FIG. 3 and described hereinabove) configured to at least slightly advance the user's mandible so that air provided by the air transmission member 40 is more efficiently provided to the user. The anchoring member 20 may be coupled to the lip sealing member 30. According to an aspect, the user's lips may be positioned between the inner lip seal 31 and the outer lip seal 32. The user's lips may be at least slightly compressed between the inner and outer lip seals 31, 32, thereby allowing air to be delivered through the air transmission member 40 and directly into the user's oral cavity. In other words, the inner and outer lips seals 31, 32 work in concert to seal the lips and at least reduce and/or inhibit leakage of air.

According to an aspect shown in FIG. 11, when the pressurized airflow machine is coupled to the hose 61 to deliver airflow to the oral device 100 (not shown in FIG. 11), the hose 61 is coupled to the machine at one end, and the hose is also coupled to receiving end 42 of the air transmission member 40 at its other end. As illustrated in FIG. 11 and in some embodiments, the oral device 100 may include a headgear 80 configured to be worn on the user's head and/or for maintaining the oral device 100 in a substantially secure position during the user's sleep. According to an aspect, the headgear 80 includes a support member 81 having four sides 82a, 82b, 82c, 82d. Each of the four sides 82a, 82b, 82c, 82d may have one of a first slot 83a, a second slot 83b, a third slot 83c, and an attachment mechanism 84. According to an aspect, the first slot 83a is opposite the second slot 83b, and the third slot 83c is opposite the attachment mechanism 84.

The headgear 80 may further include an adjustable headband 85 coupled to the support member 81. The adjustable headband 85 may include a first headband (or first strap) 85a and a second headband (or second strap) 85b, each of which has a first end 86a and a second end 86b. According to an aspect, the first end 86a of the first headband 85a is positioned in the first slot 83a, and the second end 86b of the first headband 85a is positioned in the second slot. In this manner, the first headband 85a is coupled to the support member 81 and may be extendibly positioned around a circumference of the user's head (i.e., across the forehead of the user), such that the support member 81 may be maintained in a secure position during the user's sleep. According to an aspect, the first end 86a of the second headband 85b is positioned in the third slot 83c, while the second end 86b of the second headband 85b is coupled to a portion of the first headband 85a. As illustrated in FIG. 11 and in an embodiment, the second headband 85b is extendibly positioned over and around a crown of the user's head (i.e., over the top of the user's head). However, other headband configurations are contemplated hereby.

The first and second headbands, 85a, 85b may comprise any material that may be extended around the periphery and/or top of at least a portion of the user's head, in a manner that will be comfortable to wear for extended periods of time, such as, during the user's full night's sleep. According to an aspect, the adjustable headband 85 is configured as straps that are padded, adjustable and/or stretchable to provide a comfortable fit for the user.

According to an aspect, the attachment mechanism 84 of the headgear 80 is coupled to the support member 81. The attachment mechanism 84 includes a coupling portion 87. The coupling portion 87 may be configured to receive and temporarily hold the hose 61 in a secure position. According to an aspect, the coupling portion 87 may be a claw clamp, claw, or clasp that may adjustably tightened or loosed around a circumference of the hose 61.

The components of the apparatus illustrated are not limited to the specific embodiments described herein, but rather, features illustrated or described as part of one embodiment can be used on or in conjunction with other embodiments to yield yet a further embodiment. It is intended that the apparatus include such modifications and variations. Further, steps described in the method may be utilized independently and separately from other steps described herein.

While the apparatus and method have been described with reference to specific embodiments, it will be understood by those skilled in the art that various changes may be made and equivalents may be substituted for elements thereof without departing from the scope contemplated. In addition, many modifications may be made to adapt a particular situation or material to the teachings found herein without departing from the essential scope thereof.

In this specification and the claims that follow, reference will be made to a number of terms that have the following meanings. The singular forms "a," "an" and "the" include plural referents unless the context clearly dictates otherwise. Furthermore, references to "one embodiment", "some embodiments", "an embodiment" and the like are not intended to be interpreted as excluding the existence of additional embodiments that also incorporate the recited features. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Terms such as "first," "second," "upper," "lower," etc. are used to identify one element from another, and unless otherwise specified are not meant to refer to a particular order or number of elements.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

As used in the claims, the word "comprises" and its grammatical variants logically also subtend and include phrases of varying and differing extent such as for example, but not limited thereto, "consisting essentially of" and "consisting of." Where necessary, ranges have been supplied, and those ranges are inclusive of all sub-ranges therebetween. It is to be expected that variations in these ranges will suggest themselves to a practitioner having ordinary skill in the art and, where not already dedicated to the public, the appended claims should cover those variations.

Advances in science and technology may make equivalents and substitutions possible that are not now contemplated by reason of the imprecision of language; these variations should be covered by the appended claims. This written description uses examples to disclose the method, machine and computer-readable medium, including the best mode, and also to enable any person of ordinary skill in the art to practice these, including making and using any devices or systems and performing any incorporated methods. The patentable scope thereof is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal language of the claims.

What is claimed is:

1. An oral device for treatment of sleep apnea in a user, comprising:
    an anchoring member configured to receive a dentition of the user, wherein the anchoring member comprises an aperture extending therethrough;
    an air transmission member comprising a receiving end, a delivery end spaced apart from the receiving end and connected to the anchoring member, and a passageway extending between the receiving end and the delivery end, wherein at least a portion of the delivery end is configured for being received within the user's mouth and the aperture of the anchoring member is in open communication with the passageway of the air transmission member; and
    a lip sealing member positioned on the air transmission member, the lip sealing member comprising an inner lip seal fixed on a surface of the air transmission member, and an outer lip seal having an orifice extending therethrough, wherein the outer lip seal is adjustably positioned on the air transmission member.

2. The oral device of claim 1, further comprising:
an airflow manifold positioned between the air transmission member and the anchoring member, the airflow manifold comprising a connector comprising a first end and a second end, the first end positioned along the delivery end of the air transmission member, and the second end coupled to the anchoring member.

3. The oral device of claim 1, wherein the anchoring member further comprises:
an air conduit body connected to the delivery end of the air transmission member, wherein the air conduit body includes an aperture formed therethrough, the aperture adapted to receive air from the air transmission member.

4. The oral device of claim 1, wherein the lip sealing member is customized to seal the user's lips between the inner lip seal and the outer lip seal.

5. The oral device of claim 1, wherein at least one of the inner lip seal and the outer lip seal is composed of an initially soft-moldable material that is curable into a semi-rigid material that provides a customized fit for the user.

6. The oral device of claim 1, wherein the inner lip seal is compressively secured to the air transmission member.

7. The oral device of claim 1, further comprising:
an adjustment member,
wherein the outer lip seal is received on the adjustment member, and the adjustment member is slidingly moveable in a lateral direction towards and away from the anchoring member.

8. The oral device of claim 1, wherein the anchoring member is a unitary structure configured to receive an upper dentition of a user and a lower dentition of a user.

9. An oral device for treatment of sleep apnea in a user, comprising:
an anchoring member configured to receive a dentition of the user, the anchoring member comprising an upper member for receiving an upper dentition and a lower member for receiving a lower dentition;
an air transmission member comprising a receiving end, a delivery end spaced apart from the receiving end and connected to the anchoring member, and a passageway extending between the receiving end and the delivery end;
a lip sealing member positioned on the anchoring member and comprising an inner lip seal fixed on a surface of the air transmission member and an outer lip seal having an orifice extending therethrough and adjustably positioned on the air transmission member, wherein the inner and outer lip seals are operatively configured to seal the user's lips therebetween; and
an airflow manifold positioned between the air transmission member and the anchoring member, the airflow manifold comprising a deflector channel configured to distribute the air received from the air transmission member to a plurality of openings formed in the anchoring member.

10. The oral device of claim 9, wherein the airflow manifold comprises:
a connector integrally formed with the lower member, the connector comprising:
a first end positioned along the delivery end of the air transmission member, and
a second end positioned along an outer wall of the lower member.

11. The oral device of claim 10, wherein the connector, the lower anchoring member, and the air transmission member are formed integrally with each other.

12. The oral device of claim 9, wherein the receiving end of the air transmission member is substantially perpendicular to the delivery end of the air transmission member.

13. The oral device of claim 9, wherein
the lower anchoring member further comprises a mandibular protrusion member, and
the upper anchoring member includes a bilateral displacer in engagement with the mandibular protrusion member.

14. An oral device for treatment of sleep apnea in a user, comprising:
an anchoring member configured to receive a dentition of the user, the anchoring member comprising an upper member for receiving an upper dentition, and a lower member for receiving a lower dentition, the lower member including a mandibular protrusion member;
an air transmission member comprising a receiving end, a delivery end spaced apart from the receiving end and connected to the anchoring member, and a passageway extending between the receiving end and the delivery end; and
a lip sealing member positioned on the air transmission member, the lip sealing member comprising an inner lip seal fixed on the air transmission member, and an outer lip seal comprising a central orifice extending therethrough, wherein the outer lip seal is adjustably positioned on the air transmission member and the lip sealing member is customized to seal the user's lips between the inner lip seal and the outer lip seal.

15. The oral device of claim 14, further comprising:
an airflow manifold positioned between the air transmission member and the anchoring member, the airflow manifold comprising a connector comprising a first end and a second end, the first end being positioned along the delivery end of the air transmission member and the second end positioned along an outer wall of the lower member of the anchoring member.

16. The oral device of claim 14, wherein at least one of the inner lip seal and the outer lip seal is composed of an initially soft-moldable material that is curable into a semi-rigid material that provides a customized fit for the user, and wherein the customized fit comprises the inner lip seal and the outer lip seal being customizable to the user's lips.

17. The oral device of claim 14, wherein the upper anchoring member includes a bilateral displacer configured to engage with the mandibular protrusion member to fulcrum the user's mandible anteriorly towards the opening of the user's mouth.

18. The oral device of claim 14, wherein the inner lip seal is compressively held in place on the air transmission member.

* * * * *